United States Patent
Delack

(10) Patent No.: US 7,232,830 B2
(45) Date of Patent: Jun. 19, 2007

(54) METHOD FOR TREATMENT OF NEURODEGENERATIVE DISEASES AND EFFECTS OF AGING

(76) Inventor: Elaine A Delack, 17317 E. Lake Goodwin Rd., Stanwood, WA (US) 98292

( * ) Notice: Subject to any disclaimer, the term of this patent is extended or adjusted under 35 U.S.C. 154(b) by 255 days.

(21) Appl. No.: 09/887,832

(22) Filed: Jun. 21, 2001

(65) Prior Publication Data

US 2003/0113309 A1 Jun. 19, 2003

Related U.S. Application Data

(63) Continuation-in-part of application No. 09/340,277, filed on Jun. 25, 1999, now Pat. No. 6,277,402, application No. 60/090,832, filed on Jun. 26, 1998.

(51) Int. Cl.
*A01N 43/42* (2006.01)
(52) U.S. Cl. .................................................. 514/280
(58) Field of Classification Search ................ 424/400; 514/280
See application file for complete search history.

(56) References Cited

U.S. PATENT DOCUMENTS

| | | | | |
|---|---|---|---|---|
| 4,409,243 | A | * | 10/1983 | Lieb ........................... 514/647 |
| 4,521,405 | A | | 6/1985 | McMichael |
| 4,705,685 | A | | 11/1987 | McMichael |
| 4,769,322 | A | | 9/1988 | Henry et al. |
| 7,672,577 | | * | 1/1992 | Epstein et al. |
| 5,264,459 | A | | 11/1993 | Chelmicka-Schorr |
| 5,672,622 | A | | 9/1997 | Hedgepeth et al. |
| 5,780,026 | A | | 7/1998 | Yoshii et al. |
| 5,821,259 | A | | 10/1998 | Theoharides |
| 5,889,033 | A | | 3/1999 | Kaminski |
| 6,025,395 | A | | 2/2000 | Breitner et al. |
| 6,071,889 | A | | 6/2000 | Weiss et al. |
| 6,117,912 | A | * | 9/2000 | DiSanto ....................... 514/654 |
| 6,242,492 | B1 | * | 6/2001 | Bergeron, Jr. ................ 514/566 |

FOREIGN PATENT DOCUMENTS

| | | | |
|---|---|---|---|
| GB | 903866 | A | 8/1962 |
| SU | 1640653 | * | 4/1991 |
| WO | WO 9100730 | A | 1/1991 |
| WO | WO-96/11009 | * | 4/1995 |
| WO | WO95289926 | A | 11/1995 |
| WO | WO 9802165 | A | 1/1998 |

OTHER PUBLICATIONS

Greenberg et al, b-adrenergic receptors in aging rat brain, 1978, Recent Adv. Pharmacol. Adrenoreceptors, Proc. Satell. Symp. Int. Congr. Pharmacol., 7th, 241-50.*
Management of Multiple Sclerosis—Jonez, M.D., (May 1952 pp. 415-422).
Transdermal Histamine in Multiple Sclerosis—Gilson, G., (Dec. 1999, pp. 424-428).

* cited by examiner

*Primary Examiner*—Alton Pryor
(74) *Attorney, Agent, or Firm*—Todd N. Hathaway

(57) ABSTRACT

A method for treatment of neurodegenerative disease conditions stemming from multiple sclerosis, aging, autoimmune diseases and fibromyalgia. A compound effective to increase neuronal metabolism of histamine to a histamine $H_2$ agonist is administered in an amount sufficient to stimulate production of cyclic AMP at a level which is sufficient to maintain myelin against undergoing self-degeneration. The compound is selected from the group consisting of histamine M-methyltransferase, monoamineoxidase-A, monoamineoxidase-A agonists and histamine $H_3$ antagonists. The histamine M-methyltransferase may be administered to increase neuronal metabolism of histamine to tele-methylhistamine, whereas the monoamineoxidase-A or monoamineoxidase-A agonist may be administered so as to increase neuronal metabolism of telemethylhistamine to an $H_2$ agonist. Separately or in conjunction with the others, the histamine $H_3$ antagonist may be administered so as to inhibit metabolism of the telemethylhistamine to an $H_3$ agonist, thereby increasing metabolism of the telemethylhistamine to an $H_2$ agonist. The increased histamine $H_2$ agonist levels reduce demyelination and the symptoms that are associated with these conditions.

5 Claims, No Drawings

METHOD FOR TREATMENT OF NEURODEGENERATIVE DISEASES AND EFFECTS OF AGING

This application is a continuation-in-part of copending application Ser. No. 09/340,277 filed Jun. 25, 1999, now U.S. Pat. No. 6,277,402 and claims benefit of Ser. No. 60/090,832 filed Jun. 26, 1998.

BACKGROUND a. Field of the Invention

The present invention relates generally to methods for the treatment of neurological conditions, and, more particularly, to a method for alleviating/controlling symptoms associated with neurodegeneration and similar conditions stemming from multiple sclerosis, aging, autoimmune diseases and other causes, by administration of compositions which induce an increased presence of histamine H2 and cyclic AMP in the body.

b. Related Art

Neurodegenerative conditions, which include diseases of autoimmunity, strike an increasing number of individuals each year, and for many of these conditions conventional treatments offer little in the way of true relief. In some instances, the neurodegenerative conditions are more or less specifically associated with a particular disease, such as multiple sclerosis, while in other instances the conditions are associated more generally with aging or some other condition or process of the body, such as a genetic disorder or an autoimmune disease, fibromyalgia, for example. As a group, however, these conditions are characterized by weakness and impaired physical functions, and, sometimes, impaired mental functions as well. Debilitation is often progressive, and, as stated, conventional treatments and therapies have been limited in their success.

For purposes of illustration the invention will be described below largely in the context of multiple sclerosis, which is a condition to which the invention has particular applicability; however, it will be understood that the present invention is applicable to neurodegenerative conditions, including autoimmune diseases, fibromyalgia, having any of a variety of sources, therefore it is not limited in scope to the treatment of multiple sclerosis alone.

As is known, multiple sclerosis (referred to from time-to-time hereinafter as "MS") is a chronic degenerative disease of the central nervous system, characterized by demyelination of the nerve axons. Symptoms include varying degrees of fatigue, numbness, tremors/muscle spasms and paralysis, coupled with a heightened susceptibility to heat and other environmental stressors. Currently, approximately 2,500,000 people worldwide have been diagnosed as having multiple sclerosis. Onset of the disease usually occurs between 20 and 40 years of age.

It is recognized that MS occurs in at least two general types, i.e., "remissive-relapsive", in which acute exacerbations are separated by periods of partial recovery, and "chronic-progressive", in which the symptoms continue generally unrelieved and there is a progressive deterioration of the patient's condition that may eventually result in total debilitation.

Efforts at treatment of MS have heretofore concentrated almost entirely on the body's autoimmune response system. The prevailing theory has been that some agent causes the myelin sheath to be attacked by the immune system, resulting in destruction of the myelin and creation of lesions. It is also believed that certain viruses may play a role in causing or precipitating MS: In particular, the measles virus may be involved in the disease, in that studies have not only found that people suffering from MS almost invariably possess the measles antigen, but also that MS patients generally have higher than normal levels of measles antibodies in their serum and cerebrospinal fluid. One theory has been that the measles or other virus triggers the T-cells to attack and destroy the myelin sheath.

Proceeding on the theory that MS is the result of an autoimmune response triggered by measles or another virus, most conventional treatment techniques have involved the use of Betaseron, Avonex and/or other anti-viral substances, generally referred to collectively as "Interferon". The intended purpose of these materials is to impede the RNA-DNA transcription process in the T-cells, which is believed to be triggered by the virus attacking the myelin. While interferon has demonstrated some positive results when treating remissive-relapsive type MS, it has proven almost entirely ineffective against the chronic-progressive type.

Another treatment method that has yielded a limited degree of success involves the injection of adenosine monophosphate. This material is not readily absorbed, in part because it is ordinarily available only in an oil-based solution, and is not "friendly" to the patient's tissues. The tissues have a tendency to wall off the material and form a small abscess capsule around it, and with each injection the material becomes harder and harder to absorb. In order for the material to be absorbed, most patients must walk vigorously on a treadmill for 20-30 minutes or engage in other strenuous exercise, or else the material will simply remain at the injection site with the result that the patient becomes extremely sore and the symptoms do not improve. Most people suffering from MS, however, are not mobile and are simply incapable of engaging in such exercise. Consequently, while many individuals experience significant benefits at the beginning of adenosine monophosphate treatments, these results eventually fade as the person's body becomes unable to absorb the material.

As will be described in greater detail below, the present invention is not postulated on conventional autoimmune theories, and instead enhances neuronal metabolism of histamine to its H2 agonist in order to prevent/repair self-degeneration of the myelin. With the exception of experimental studies by Hinton D. Jonez, M.D. (Jonez, "Management of Multiple Sclerosis", Postgraduate Medicine, May 1952) and certain methods described in patents to John McMichael (U.S. Pat. Nos. 4,521,405 and 4,705,685), histamine phosphate (which is most commonly employed for diagnosis of stomach conditions) has not been used in connection with multiple sclerosis and related disorders.

The work of both Jonez and McMichael is founded on conventional autoimmune response theories. Dr. Jonez's experiments in the early 1950's attempted to manipulate the body's allergic responses using histamine phosphate, and also used the material as a vasodilator to get more blood to the brain and other parts of the nervous system. In this context, it should be understood that the present invention employs histamine phosphate to mimic histamine H2, the functions of which are confined mainly to the central nervous system, whereas the primary agent in allergic reactions is histamine H1. At the time of Dr. Jonez's work, however, this distinction (between histamine H1 and histamine H2) was not fully appreciated.

McMichael's method involves the injection of a small amount of an "immunogen" consisting of viral fragments or other antigens (under the theory known as "provocative neutralization"), together with a small amount of histamine phosphate. McMichael identifies histamine phosphate as a vasodilator, and theorizes that the histamine phosphate reacts with the immunogen to form an "active complex" which affects absorption of the material. In any event, the amounts of histamine phosphate that are involved in McMichael's treatment are far too small to have any significant impact on overall levels of histamine H2 in the body.

As was noted above, many other neurodegenerative conditions besides MS are widespread in the population. Many of these conditions are associated with the aging process and are therefore becoming increasingly common as the numbers of elderly increase in the United States and many other countries. Some of these conditions have been conventionally approached on a similar basis to the autoimmune theories described above, and again with limited success. Most other approaches have been similarly disappointing, and in many instances progression of the neurodegenerative conditions has simply been accepted as inevitable.

Accordingly, there exists a need for a treatment method that effectively alleviates the symptoms of multiple sclerosis and other neurodegenerative disease conditions. Furthermore, in the specific case of MS, there exists a need for such a method that provides an effective treatment for both the remissive-relapsive and chronic-progressive forms of the disease. Still further, there exists a need for such a method in which the treatment compositions are readily absorbed into the patient's body, without requiring resort to physical exercise for effective absorption. Still further, there exists a need for such a method that is sufficiently economical to be widely available to the large number of individuals who suffer from MS and other neurodegenerative diseases.

SUMMARY OF THE INVENTION

The present invention addresses the problems cited above, and is a method for treatment of neurodegenerative disease conditions stemming from multiple sclerosis, aging, autoimmune diseases, and fibromyalgia, the method broadly comprising the step of administering to a patient a compound effective to increase neuronal metabolism of histamine to a histamine $H_2$-agonist, in an amount sufficient to stimulate production of cyclic AMP at a level which is sufficient to maintain myelin against undergoing self-degeneration.

The method may further comprise the step of selecting the compound from the group consisting of histamine N-methyltransferase, monoamine oxidase-A, monoamine oxidase-A agonists and histamine $H_3$ antagonists.

The compound may comprise histamine N-methyltransferase, and the step of administering the compound may comprise administering histamine N-methyltransferase to the patient so as to increase neuronal metabolism of histamine to tele-methylhistamine. The step of administering histamine N-methyltransferase may comprise administering isolated histamine N-methyltransferase by injection.

In another embodiment, the compound may be monoamine oxidase-A, and the step of administering the compound may comprise administering monoamine oxidase-A to the patient so as to increase neuronal metabolism of tele-methylhistamine to an $H_2$ receptor agonist such as 4-methylhistamine.

In another embodiment, the compound may be a monoamine oxidase-A agonist, and the step of administering the compound may comprise administering the monoamine oxidase-A agonist to the patient so as to increase neuronal metabolism of tele-methylhistamine to an $H_2$ agonist such as 4-methylhistamine. The monoamine oxidase-A agonist may be reserpine, and the step of administering the monoamine oxidase-A agonist may comprise administering reserpine by slow-release transdermal dose. Alternatively, the step of administering the monoamine oxidase-A agonist may comprise administering reserpine by injection, preferably in the range from about 1-10 mg/kg S.C. per day.

In another embodiment, the compound may be a histamine $H_3$ antagonist, and the step of administering the compound may comprise administering a histamine $H_3$ antagonist to the patient so as to inhibit neuronal metabolism of tele-methylhistamine to an $H_3$ agonist such as R-alpha-methylhistamine and thereby increase neuronal metabolism of the tele-methylhistamine to an $H_2$ agonist such as 4-methylhistamine. The histamine $H_3$ antagonist may be thioperamide maleate.

These and other features and advantages of the present invention will be apparent from a reading of the following detailed description.

DETAILED DESCRIPTION

The present invention provides a method for treatment of MS and other neurodegenerative conditions, i.e., autoimmune diseases, fibromyalgia, and also of certain related conditions and symptoms usually associated with aging, by stimulating increased cyclic AMP production via increased histamine H2 levels, by application of a histamine H2 agonist so as to compensate for the depleted histamine H2 levels, or by increasing neuronal metabolism of histamine in order to produce increased histamine H2 levels. The increased histamine metabolism is achieved by increasing the activity levels of histamine N-methyltransferase (HMT) or monoamine oxidase-A (MOA-A), or both.

a. Hypothesis

While not intended to be binding with respect to the practice or scope of the present invention, a hypothesis has been developed which explains the results and that have been observed in connection with the treatment described herein.

As was noted above, the conventional theory has been that demyelination is the result of an autoimmune response. However, it is also known that the integrity of the nervous system is highly dependent on cyclic AMP, in that cyclic AMP stimulates the synthesis of myelin components by oligodendrocytes and Schwann cells. Studies have shown that oligodendrocytes will undergo self-induced degeneration in the absence of cyclic AMP, resulting in demyelination, but that the degenerating cells will again become viable and capable of synthesizing myelin if treated with cyclic AMP (e.g., see Kim, "Neurobiology of human oligodendrocytes in culture", J. of Neuroscience Research, Dec. 27, 1990).

Cyclic AMP, in turn, is produced naturally in brain tissue, largely in the pineal gland. In the case of persons suffering from MS, especially in the chronic-progressive phase, the levels of histamine H2 have been observed to be very low, and the pineal gland functions tend to be atrophied. It is also known that production of cyclic AMP by the pineal gland is controlled to a large extent by the presence of histamine H2 in the blood stream. Histamine H2 (as differentiated from histamine H1) is produced by cells in the central nervous system, particularly those in the hypothalamus. In other words, certain cells within the central nervous system produce the histamine H2 that stimulates the pineal gland to produce cyclic AMP, which in turn is essential to protect the myelin against self-degeneration.

It is Applicant's hypothesis that in persons suffering from MS and similar neurodegenerative conditions, the histamine H2-producing cells in the central nervous system are damaged or impaired, possibly by one or more strains of the measles virus, so that over time these cells reduce or cease production of histamine H2, or of the enzymes that are essential to the production of histamine H2. Inadequate production of histamine H2, in turn, results in greatly reduced output of cyclic AMP from the pineal gland, leading ultimately to self-degeneration of the myelin. Hence, under Applicant's hypothesis, the lesions do not result directly from an autoimmune attack on the myelin, but are instead the result of self-degeneration of the myelin precipitated by damage or impairment of the histamine H2-producing cells of the central nervous system.

It is further hypothesized, at least in the case of MS, that the damage is progressive, in that the remissive-relapsive form of the disease represents an earlier phase in which the cells are subjected to ongoing attack but some capacity to produce histamine H2 remains, while the chronic-progressive form represents a subsequent phase in which the capacity to produce histamine H2 is essentially eliminated.

Applicant's hypothesis is consistent with prior observations concerning attempted treatments for the disease. For example, as was noted above, MS symptoms tend to respond favorably to treatment with interferon and other anti-viral agents when the disease in the remissive-relapsive phase, but such treatments become ineffective when the disease enters the chronic-progressive phase. This pattern is consistent with the above hypothesis, since the interferon serves to inhibit viral replication in virus-infected cells and therefore slows damage to the remaining histamine H2-producing cells during the remissive-relapsive phase, but when the disease has reached the chronic-progressive phase virtually all of the histamine H2 producing cells have been destroyed or impaired, so that further interferon treatments can have no effect on histamine H2 output.

Additional corroborating evidence includes observations that the histamine H2 levels of MS patients in the remissive-relapsive phase tend to fluctuate, sometimes being abnormally high and at other times being abnormally low. This observation is also consistent with the above hypothesis, in that it will be understood that as viruses replicate and spread they cause physical disruption of cellular structures, i.e., the cells become filled with replicated virus and ultimately "explode", releasing their contents into the blood stream. In the case of histamine H2-producing cells, these contents would include not only replicated virus bodies, but also the histamine H2 contained in the cell, which may account for the sometimes increased levels of histamine H2 which are observed during periods of exacerbation in the remissive-relapsive phase.

Furthermore, histamine H2 is a known heat stress modulator, and inability to handle heat stress (reflecting a low level of histamine H2) is a classic symptom of MS. Histamine H2 is also believed to regulate the number of T-cells in the body, and research has shown that people with MS tend to have abnormally low numbers of T-cells during periods of exacerbation.

A number of other conditions exhibit symptoms similar to those in MS. Some of these, such as Parkinson's disease and Alzheimer's disease, are neurodegenerative diseases. Other conditions are associated more generally with the aging process (or sometimes genetic disorders or fibromylgia), and may not necessarily involve demyelination per se. Many of the latter conditions produce one or more symptoms similar to those of MS, but often to a lesser degree or without the presence of all of the symptoms that are associated with actual demyelination. Applicant hypothesizes that many of these conditions may stem from a common source, i.e., a reduced production or presence of histamine H2. In short, it is believed that certain of these conditions and symptoms, especially the less acute ones associated with the aging process, reflect a moderately depressed production or presence of histamine H2, while more severely reduced histamine H2 levels lead to demyelination and the severe symptoms associated with the neurodegenerative diseases.

This hypothesis correlates with the results of other recent research. For example, it has been found that aging results in vascular changes due to alterations in endothelial cells and vascular tone regulation. These changes result in hypertension, coronary artery disease, heart failure, and postural hypotension (Marin & Rodriguez-Martinez, Exp Gerontol, July 1999, 34:503-12). H2 receptor stimulation regulates the contractility of the small-diameter arteries (Fernandez et al., Acta Physiol Scan, August 1994, 151:441-51). H2 receptor activation of the Na+/K+/ATPase system stimulates nitric oxide production, which leads to endothelial relaxation in small-diameter arteries (Garcia-Villaon et al., J Pharm Pharmacol, October 1996, 48:1057-62). The Na+ pump activity is stimulated by the Na+/K+/ATPase system, which is activated by H2 receptor stimulation. Na+/K+/ATPase inhibition, such as by ouabian, inhibits the Na+ pump. Thus, deficient H2 stimulation is implicated in decreased Na+ pump activity and the related symptoms. Research confirms that the Na+ pump activity is reduced in aging (Marin & Rodriguez-Martinez, 1999).

Vascular calcium (Ca(2+)) homeostasis is also altered in aging. Extracellular Ca(2+) dependence on contractile responses of the endothelium is enhanced, thus the elderly have increased sensitivity to Ca(2+) antagonists (Marin & Rodriguez-Martinez, 1999). Histamine treatment decreases the release of Ca(2+) from intracellular stores, thus decreasing the contractile responses of the endothelium (Song et al., Eur J Pharmacol, March 1997, 19;322:265-73).

H2 receptor stimulation also increases gastric acid secretion and digestive enzyme production. Research shows that gastric acid secretion decreases about 30% in the elderly, and that production of digestive enzymes such as pepsin is reduced by approximately 40% in the elderly (Feldman et al., Gastroenterology, April 1996, 110:1043-52). Again, reduced H2 levels are implicated.

Still further, it has been demonstrated that aging modifies the basal and stress-stimulated functions of the hypothalamic presynaptic histamine neurons (Ferretti et al., Pharmacol Biochem Behav, January 1998, 59:255-60). These changes in the histaminergic systems in connection with aging may explain the sleep disturbances and immune system suppression that are common in the elderly: H2 agonists stimulate the pineal gland to produce cAMP and melatonin. Melatonin is involved in the Rapid Eye Movement (REM) stage of sleep which is often deficient in the elderly, which can lead to cognitive and memory defects (Schredl et al., Exp Gerontol, February 2001, 36:353-61). Cyclic AMP, in turn, is involved in boosting the immune system response, as has been discussed above.

Therefore, although the invention is described herein largely with reference to the example of multiple sclerosis, it will be understood that the present invention may be also be employed in the treatment of similar conditions that are associated with aging or other causes, where the root problem lies in deficient levels of histamine H2. For example, in addition to MS, Parkinson's disease and Alzheimer's disease, the present invention may be used to treat various other conditions and disorders of the types noted above, including conditions relating to pineal gland, thymus and thyroid functions, gastric disorders, hypertension, and sleep and memory disorders.

b. Histamine H2 Augmentation

For the reasons explained above, it is believed that MS and similar neurodegenerative conditions, as well as certain other symptoms associated with aging, are precipitated by the body's inability to produce adequate levels of histamine H2. Consequently, one embodiment of the present invention employs histamine phosphate or selected beta-adrenergic agents to replace or "mimic" the histamine H2, in an amount that is sufficient to induce increased production of cyclic AMP (i.e., by the pineal gland), at levels that are adequate to eliminate and/or repair the self-degeneration of the myelin. The purpose of the caffeine or other phosphodiesterase inhibitor, in turn, is to reduce the action of phosphodiesterase (the enzyme in the human body which breaks down cyclic AMP), thereby providing higher cyclic AMP levels over longer periods of time without having to rely on excessively high dosages of histamine phosphate.

Histamine phosphate is generally preferred as the histamine H2 analogue component in the present invention because of its wide availability and comparatively low cost, and because it very effectively mimics the action of the body's natural histamine H2 (e.g., see Fact and Comparisons, January 1988). Moreover, in addition to stimulating production of cyclic AMP, the histamine phosphate helps to provide stress modulation, again similar to the natural histamine H2.

Histamine phosphate is most commonly supplied in the form of histamine diphosphate. A suitable source of histamine phosphate for use in the present invention is a solution available from Eli Lily and Company as "histamine phosphate injection, U.S.P."; this material is currently recognized by the US Food and Drug Administration (FDA) for use as a gastric acid test. Other suitable compounds that mimic the presence of histamine H2 for purposes of stimulating cyclic AMP production by the pineal gland may be used in the method of the present invention, either in combination with or in place of the histamine phosphate. For example, isoproterenol and/or other beta-adrenergic agents that are known or determined to be histamine H2 mimicking agents may be used in this component.

Similarly, caffeine is a preferred choice for the phosphodiesterase inhibitor because of its low expense and long half-life, in addition to its comparatively minimal side effects and wider therapeutic index. Other suitable phosphodiesterase inhibitors may also be used in accordance with the present invention to enhance the production of cyclic AMP, however, such as theophylline, theophylline derivatives, and other methylxanthine agents. As was noted above, the purpose of this component is to enhance the effect of the increased levels of cyclical AMP that are produced by the histamine H2 analog, by conserving the cyclical AMP against breakdown by the phosphodiesterase enzymes. In the absence of the phosphodiesterase inhibitor component, much higher levels of histamine phosphate would be required to achieve the same result, increasing the risk of adverse cardiovascular reactions and other negative side effects.

Caffeine citrate is generally preferred for the caffeine component in transdermal applications, due to its solubility and ability to achieve high concentrations in transdermal gel. Also, it should be noted that references to amounts and dosages of caffeine herein refer to measures of caffeine base (i.e., the caffeine molecule), and do not include other materials that are sometimes found associated with the caffeine in a commercially available product.

The treatment composition may be administered by any suitable means, such as orally or by transdermal patch, subcutaneous injection, intravenous injection, or inhaler, to give just a few examples. Administration by transdermal patch may be preferable in many embodiments, in that this provides significant advantages in terms of ease of use and consistent dosage levels. As used in this description and appended claims, the term "transdermal patch" includes both adhesive patches and other systems and devices for transdermal administration of treatment compositions.

The following illustrative examples relate to actual practice of the invention described above in the alleviation of the symptoms of MS patients.

EXAMPLE ONE

A 39 year old, 144-pound female patient clinically diagnosed as suffering from multiple sclerosis was treated in accordance with the method of the present invention. The patient had suffered from Multiple Sclerosis for approximately 12 years prior to treatment, and exhibited symptoms indicating that the disease had advanced to the chronic-progressive phase. Approximately 0.069 milligrams of histamine phosphate solution (Eli Lily & Co., see above) were administered subcutaneously three times daily, accompanied by simultaneous oral administration of approximately 200 milligrams of caffeine in aqueous solution. Clinically significant improvements were observed within 24 hours, and full mobility was regained in about two days. The patient subsequently continued the treatment regimen, with no additional exacerbation episodes having occurred to date.

EXAMPLE TWO

Ten patients participating in clinical trials were treated in accordance with the present invention. The patients were selected from a larger group of candidates on the following basis:
  (a) Each was clinically diagnosed as suffering from multiple sclerosis;
  (b) Each was diagnosed as being in the "chronic-progressive" phase of the disease, so as to minimize the possibility of erroneous results due to spontaneous remission; and
  (c) Each was assessed as exhibiting physical deterioration in the range from about 5.0 to 7.5 on the MS Expanded Disability Status Scale (EDSS), so that the disability would be severe enough that an improvement in condition would be clinically noticeable, but not so severe that the musculatory structure would have atrophied to the point where no improvement could be observed even if neurological damage was reversed.

Transdermal patches were used to administer the treatment compositions, as opposed to the subcutaneous/oral regimen described in Example One. Each patch was used for an 8-hour period and contained approximately 1.1 mg of histamine diphosphate and 100 mg of caffeine citrate, dissolved in approximately 0.2 mil of transdermal gel. The gel was deposited on the patch in an area approximately 6 mm in diameter, so as to minimize the area of potential skin irritation. The patch was both air and light occlusive, in order to protect the treatment material from decomposition.

Each patient's condition was assessed at the commencement of the trial to establish a baseline score. The assessments were performed using the following standard tools:

(1) MS-Related Symptoms checklist (MS-RS), (2) Fatigue Severity Scale (FSS), (3) Kurtzke Functional Systems tool (FS), and (4) the EDSS scale. The assessment was repeated after forty-five (45) days of treatment, and again at the ninety (90) day point.

The assessment tools listed above will be familiar to those skilled in the relevant art. For purposes of illustration, however, each will be summarized below, together with representative data produced during the trial.

The MS-RS tool is a self-reporting system which utilizes a 6-point Likert scale (0=never, 5=always) that measures the prevalence of symptoms involving the following: Fine and gross motor (arm and leg weakness, spasms, tremors, balance problems); brainstem (vision problems, memory impairment, dysphagia); sensory pain (pain, burning sensations, tingling); mental (anxiety, depression); elimination (urine frequency and urgency). An example MS-RS report for one of the patients in the trial is set forth below:

MS STUDY

Respondent No: 4337
MR-RS (Self-reporting)
Please indicate how frequently you experience each of the symptoms using the following scale:

Never ⊢—⊢—⊢—⊢—⊢—⊣ Always
0   1   2   3   4   5

|  | Base Line | 45 days | 90 days |
| --- | --- | --- | --- |
| Arm weakness | 5 | 2 | 0 |
| Leg weakness | 5 | 2 | 3 |
| Spasms | 5 | 4 | 2 |
| Tremors | 4 | 3 | 1 |
| Knee locking | 3 | 1 | 1 |
| Balance problems | 4 | 1 | 0 |
| Falling | 3 | 0 | 0 |
| Urine frequency: day | 3 | 2 | 0 |
| Urine frequency: night | 3 | 2 | 0 |
| Trouble making bathroom: day | 1 | 0 | 0 |
| Trouble making bathroom: night | 1 | 0 | 0 |
| Loneliness | 0 | 0 | 0 |
| Depression | 3 | 2 | 2 |
| Anxiety | 2 | 2 | 0 |
| Pain | 4 | 3 | 4 |
| Burning | 0 | 0 | 0 |
| Numbness | 4 | 2 | 1 |
| Pins and needles | 5 | 3 | 1 |
| Double vision | 4 | 4 | 2 |
| Blurred Vision | 4 | 3 | 2 |
| Difficulty swallowing | 1 | 2 | 0 |
| Forgetfulness | 3 | 4 | 0 |

The FSS tool provides a quantitative measure of fatigue, which is a prominent complaint of MS patients. The FSS tool employs a 1 to 7 Likert scale (1=strongly disagree, 7=strongly agree), and is also a self reporting system. An example FSS report, for the same patient as in the previous example, is set forth below:

MS STUDY

Respondent No: 4337
FSS (Self-reporting)
Please indicate to what extent you agree or disagree with the following statements using the scale:

Strongly Disagree ⊢—⊢—⊢—⊢—⊢—⊢—⊢—⊣ Strongly Agree
0   1   2   3   4   5   6   7

|  |  | Baseline | 45 days | 90 days |
| --- | --- | --- | --- | --- |
| 1. | My motivation is lower when I am fatigued | 7 | 5 | 5 |
| 2. | Exercise brings on my fatigue | 5 | 4 | 5 |
| 3. | I am easily fatigued | 6 | 5 | 1 |
| 4. | Fatigue interferes with my physical functioning | 6 | 5 | 1 |
| 5. | Fatigue causes frequent problems for me | 6 | 3 | 1 |
| 6. | My fatigue prevents sustained physical functioning | 5 | 3 | 2 |
| 7. | Fatigue interferes with carrying out certain duties and responsibilities | 6 | 2 | 1 |
| 8. | Fatigue is among my three most disabling symptoms | 4 | 4 | 3 |
| 9. | Fatigue interferes with my work, family, or social life | 3 | 2 | 1 |

The FS tool provides an objective measurement of neurological impairment in the following systems: pyramidal, cerebellar, brain stem, sensory, bowel/bladder, optic and mental. The data is physician-reported, as opposed to the self-reporting systems used in the MS-RS and FSS tools. The cumulative FS data for the trial is set forth in the following table:

CUMULATIVE TEST DATA
Functional Systems (FS)

| Patient |  | Pyramidal | Cerebellar | Brain Stem | Sensory | Bowel Bladder | Optic | Mental | Other |
| --- | --- | --- | --- | --- | --- | --- | --- | --- | --- |
| 1. 4344 | Baseline | 2 | 5 | 0 | 1 | 0 | 0 | 3 | 0 |
|  | 45 days | 2 | 5 | 0 | 1 | 0 | 0 | 3 | 0 |
|  | 90 days | 2 | 5 | 0 | 1 | 0 | 0 | 3 | 0 |
| 2. 4337 | Baseline | 3 | 2 | 3 | 1 | 0 | 2 | 1 | 0 |
|  | 45 days | 3 | 2 | 3 | 1 | 0 | 2 | 1 | 0 |
|  | 90 days | 1 | 1 | 1 | 0 | 0 | 1 | 1 | 0 |

-continued

CUMULATIVE TEST DATA
Functional Systems (FS)

| Patient | | Pyramidal | Cerebellar | Brain Stem | Sensory | Bowel Bladder | Optic | Mental | Other |
|---|---|---|---|---|---|---|---|---|---|
| 3. | 4366 Baseline | 2 | 2 | 0 | 0 | 3 | 1 | 0 | 0 |
| | 45 days | 2 | 2 | 0 | 0 | 3 | 1 | 0 | 0 |
| | 90 days | 1 | 2 | 0 | 0 | 2–3 | 1 | 0 | 0 |
| 4. | 4339 Baseline | 3 | 1 | 2 | 0 | 2 | 2 | 2 | 0 |
| | 45 days | 3 | 1 | 2 | 0 | 2 | 2 | 2 | 0 |
| | 90 days | 3 | 1 | 2 | 0 | 2 | 2 | 2 | 0 |
| 5. | 4336 Baseline | 4 | 3 | 1 | 2 | 6 | 3 | 0 | 0 |
| | 45 days | 2 | 2 | 1 | 2 | 6 | 3 | 0 | 0 |
| | 90 days | 2 | 2 | 1 | 2 | 6 | 3 | 0 | 0 |
| 6. | 4338 Baseline | 4 | 3 | 2 | 3 | 2 | 3 | 0 | 0 |
| | 45 days | 4 | 3 | 2 | 3 | 2 | 3 | 0 | 0 |
| | 90 days | 4 | 3 | 2 | 3 | 2 | 3 | 0 | 0 |
| 7. | 4341 Baseline | 3 | 0 | 0 | 2 | 1 | 0 | 0 | 0 |
| | 45 days | 3 | 0 | 0 | 2 | 1 | 0 | 0 | 0 |
| | 90 days | 3 | 0 | 0 | 2 | 1 | 0 | 0 | 0 |
| 8. | 4424 Baseline | 4 | 0 | 0 | 0 | 2 | 3 | 0 | 0 |
| | 45 days | 4 | 0 | 0 | 0 | 2 | 3 | 0 | 0 |
| | 90 days | INCOMPLETE | | | | | | | |
| 9. | 4340 Baseline | 4 | 3 | 0 | 2 | 5 | 3 | 0 | 0 |
| | 45 days | 4 | 2 | 0 | 2 | 5 | 3 | 0 | 0 |
| | 90 days | 4 | 2 | 0 | 2 | 5 | 3 | 0 | 0 |
| 10. | 4550 Baseline | 2–3 | 0 | 0 | 1 | 3 | 0 | 0 | 0 |
| | 45 days | 2–3 | 0 | 0 | 1 | 3 | 0 | 0 | 0 |
| | 90 days | 2–3 | 0 | 0 | 0 | 3 | 0 | 0 | 0 |

Finally, the EDSS scale measures progressive disability in increments of 0.5, where 0 represents normal and 10 indicates death due to MS. For reference, the portion of the EDSS scale which encompasses the conditions of subjects participating in the trial is reproduced below:

EXPANDED DISABILITY STATUS SCALE (EDSS)

Scale:
4.5=Fully ambulatory without aid, up and about much of the day, able to work a full day, may otherwise have some limitation of full activity or require minimal assistance; characterized by relatively severe disability, usually consisting of one FS grade 4 (others 0 or 1) or combinations of lesser grades exceeding limits of previous steps. Able to walk without aid or rest for some 300 meters.
5.0=Ambulatory without aid or rest for about 200 meters; disability severe enough to impair full daily activities (e.g., to work full day without special provisions). (Usual FS equivalents are one grade 5 alone, others 0 or 1; or combinations of lesser grades usually exceeding specifications for step 4.0.)
5.5=Ambulatory without aid or rest for about 100 meters; disability severe enough to preclude full daily activities. (Usual FS equivalents are one grade 5 alone, others 0 or 1; or combinations of lesser grades usually exceeding those for step 4.0.)
6.0=Intermittent or unilateral constant assistance (cane, crutch, or brace) required to walk about 100 meters with or without resting. (Usual FS equivalents are combinations with more than two FS grade 3+.)
6.5=Constant bilateral assistance (canes, crutches, or braces) required to walk about 20 meters without resting. (Usual FS equivalents are combinations with more than two FS grade 3+.)
7.0 Unable to walk beyond about 5 meters even with aid, essentially restricted to wheelchair wheels self in standard wheelchair and transfers alone; up and about in w/c some 12 hours a day. (Usual FS equivalents are combinations with more than one FS grade 4+; very rarely, pyramidal grade 5 alone.)
7.5—Unable to take more than a few steps; restricted to wheelchair; may need aid in transfer; wheels self but cannot carry on in standard wheelchair a full day; may require motorized wheelchair. (Usual FS equivalents are combinations with more than one FS grade 4+.)

Cumulative EDSS data for the trial is set forth in the following table:

Cumulative Test Data
Expanded Disability Status Scale (EDSS)

| | Patient | Baseline Score | 45 Days Score | 90 Days Score |
|---|---|---|---|---|
| 1. | 4344 | 5.0 | 5.0 | 5.0 |
| 2. | 4337 | 6.0 | 5.5 | 5.0 |
| 3. | 4366 | 6.0 | 6.0 | 6.0 |
| 4. | 4339 | 6.0 | 6.0 | 6.0 |
| 5. | 4336 | 6.0 | 5.0 | 5.0 |
| 6. | 4338 | 6.5 | 6.5 | 6.5 |
| 7. | 4341 | 6.0 | 6.0 | 6.0 |
| 8. | 4424 | 7.5 | 7.5 | Inc. |
| 9. | 4340 | 7.0 | 7.0 | 7.0 |
| 10. | 4550 | 6.0–6.5 | 6.0 | 6.0 |

As was noted, the full assessment was performed at the beginning of the trial and then repeated at the 45 and 90-day points. The overall results, showing the data acquired using the test tools described above, are set forth in the following Table A:

TABLE A

| Pt. # | MS-RS TOOL B | MS-RS TOOL 45 D | MS-RS TOOL 90D | FSS TOOL B | FSS TOOL 45 D | FSS TOOL 90D | FS TOOL B | FS TOOL 45 D | FS TOOL 90D | EDSS B | EDSS 45 D | EDSS 90D | Qualitative |
|---|---|---|---|---|---|---|---|---|---|---|---|---|---|
| 4344 | 51 | 55.5 | 44 | 57 | 56 | 55 | 11 | 11 | 11 | 5.0 | 5.0 | 5.0 | NO CHANGE |
| 4337 | 67 | 42 | 19 | 47 | 31 | 20 | 12 | 12 | 5 | 6.0 | 5.5 | 5.0 | Improved ambulation No longer using cane Increase left side strength |
| 4366 | 31 | 7 | 28 | 45 | 36 | 33 | 8 | 8 | 7 | 6.0 | 6.0 | 6.0 | Increased energy Improved ambulation Improved bladder function Reports overall improved |
| 4339 | 23 | 33 | 31 | 46 | 54 | 48 | 12 | 12 | 12 | 6.0 | 6.0 | 6.0 | NO CHANGE |
| 4336 | 47 | 30 | 27 | 50 | 33 | Inc | 19 | 16 | 16 | 6.0 | 5.0 | 5.0 | Increased energy Improved ambulation No longer using cane Increased sense of well being |
| 4338 | 58 | 50 | 56 | 29 | 25 | 41 | 17 | 17 | 17 | 6.5 | 6.5 | 6.5 | Reports overall improved Improved vision Improved writing function Imp. bladder function Improved balance Improved sexual function |
| 4341 | 34 | 28 | 31 | 33 | 38 | 45 | 6 | 6 | 6 | 6.0 | 6.0 | 6.0 | Increased energy Imp. sleeping at night |
| 4424 | 63 | 53 | Inc | 56 | 63 | Inc | 9 | 9 | Inc | 7.5 | 7.5 | Inc | Improved bladder function |
| 4340 | 56 | 39 | 41 | 49 | 26 | 28 | 17 | 16 | 16 | 7.0 | 7.0 | 7.0 | Decrease in ataxia Improved speech, first time able to sing in 18 years Increased energy Improved right arm function |
| 4550 | 46 | 33 | Inc | 54 | 37 | Inc | 7 | 7 | Inc. | 6.5 | 6.5 | Inc | Increased energy Improved speech Imp. thought process Improved sensory function |
| | most disabled score 110 | least disabled score 0 | | most disabled score 63 | least disabled score 9 | | most disabled score 40 | least disabled score 0 | | most disabled score 10.0 | least disabled score 0 | | |

Key:
B = Baseline score
45 D = 45 days on Tx score
90D = 90 days on Tx score

A review of the data in Table A shows that roughly 80% of the subjects reported a qualitative improvement in their condition as a result of the treatment, and roughly 30% exhibited an improvement of one or more levels on the EDSS scale (see patient numbers 4337, 4336 and 4550). The MS-RS tool, FSS tool and FS tool, in turn, appear to show measurable improvement in about 40% of the patients (see patient numbers 4337, 4366, 4336 and 4340).

It should be noted that, in contrast to the general pattern of trials and studies associated with interferon treatments, the trial set forth in Example Two recorded actual improvement in the condition of a significant number of the subjects, rather than simply a slowing in the rate of deterioration. In other words, while treatment methods based on the autoimmune theory have measured "success" in terms of slowing progression of MS, the clinical trial of the present invention demonstrated an apparent reversal of the effects of the disease.

Furthermore, it should be noted that the trial was conducted using essentially the smallest dose of histamine phosphate judged likely to produce observable results. Based on the study results and post-trial testing, it has been determined that an average 8-hour transdermal dose of about 1.65 mg histamine phosphate generally proves more effective. 8-hour transdermal dosages of about 2.2 mg have been tested on an individual basis, and in some instances dosages of 3.0 mg or higher may be suitable.

Based in part on the above examples, and using the preferred constituents of histamine phosphate and caffeine, the following approximate parameters are believed to cover the majority of dosages suitable for use with physically typical patients suffering from relatively advanced MS and similar neurodegenerative conditions. It will be understood, however, that the actual dosages will vary with certain factors, including the individual's weight, physical condition, and environmental and mental stressors, for example.

EXAMPLE DOSE RANGES

| Caffeine: | |
|---|---|
| Oral form (time release preferred): | 600 mg–2500 mg qd |
| Transdermal: | 6–40 mg/hr |
| Histamine phosphate: | |
| Intravenous: | 0.01–2.75 mg qd-qid |
| Subcutaneous: | |
| Injection: | 0.001–0.04 mg/kg qd-qid |
| Transdermal: | 0.13–0.63 mg/hr |

EXAMPLE 8-HOUR TRANSDERMAL DOSE RANGES (in 0.2 mil transdermal gel):

| Histamine Phosphate: | 1.0–5.0 mg |
|---|---|
| Caffeine (Caffeine Citrate): | 50–300 mg | c. Histamine Metabolite Manipulation

As stated above, it is believed that the neurodegenerative diseases and conditions to which the present invention is directed stem from or relate to inadequate production of histamine H2. In the embodiment that has been described above, histamine H2 levels are augmented directly, by administration of a histamine H2 agonist. The embodiments which are described below, in turn, achieve increased histamine H2 levels through manipulation of neuronal metabolism of the histamine H2 precursor compounds, by increasing the activity levels of histamine N-methyltransferase (HMT) or mono amineoxidase-A (MOA-A), or both.

By way of background, a study of 29 MS patients was conducted using the embodiment of the invention described in the preceding section. The study results showed significant improvement in fatigue and cognitive functions; however, the study also revealed that whole blood histamine (as distinguished from histamine H2) levels first increased and then declined to approximately baseline levels, although the improvement in symptoms persisted. Notably, 80% of those patients who saw the most improvement in the majority of areas tested had a whole blood level of histamine that was less than their baseline level at the end of the 90-day study. The following Table B sets forth the measured histamine levels for the entire study group, with those patients who received a placebo being indicated by an asterisk (*):

TABLE B

WHOLE-BLOOD HISTAMINE LEVELS

| | Patient # | Baseline | 30 Day | 60 Day | 90 Day |
|---|---|---|---|---|---|
| | 1 | 616 | 1829 | 894 | — |
| * | 2 | 867 | 821 | 871 | 779 |
| * | 3 | 755 | 854 | 957 | 726 |
| * | 4 | 350 | 451 | 224 | 420 |
| | 5 | 462 | 509 | Dropped out | — |

TABLE B-continued

WHOLE-BLOOD HISTAMINE LEVELS

| | Patient # | Baseline | 30 Day | 60 Day | 90 Day |
|---|---|---|---|---|---|
| | 6 | 398 | 562 | 314 | 415 |
| | 7 | 425 | 652 | 216 | 283 |
| | 8 | 369 | 689 | 291 | — |
| | 9 | 945 | 975 | 912 | 961 |
| | 10 | 462 | 461 | 474 | 517 |
| | 11 | — | — | — | — |
| * | 12 | 262 | 238 | Dropped out | — |
| | 13 | — | — | — | — |
| | 14 | 373 | 816 | 348 | 370 |
| | 15 | — | — | — | — |
| * | 16 | 234 | 1156 | 3480 | — |
| | 17 | 408 | 632 | 722 | 559 |
| | 18 | 524 | 595 | 598 | 600 |
| | 19 | — | — | — | — |
| * | 20 | 324 | 662 | 280 | 332 |
| | 21 | 571 | 1718 | 806 | 813 |
| | 22 | 318 | — | 239 | 291 |
| | 23 | 486 | 1080 | 257 | 396 |
| | 24 | 153 | 202 | 157 | 126 |
| | 25 | 201 | 315 | 98 | 155 |
| | 26 | 387 | 809 | 201 | — |
| | 27 | 493 | 855 | 290 | 497 |
| | 28 | — | — | — | — |
| | 29 | 318 | 415 | 215 | 284 |
| | 30 | 941 | 1894 | 2898 | 1055 |
| | 31 | — | — | — | — |
| | 32 | 228 | 251 | 189 | 247 |
| | 33 | 319 | 459 | Dropped out | — |
| | 34 | — | — | — | — |
| | 35 | 599 | 934 | 618 | 606 |
| * | 36 | 653 | 805 | 882 | 911 |

* Placebo = Citric acid and vanishing cream

It is hypothesized from the above data (indicating that those individuals having the lowest histamine levels demonstrated the most improvement) that the underlying problem is not in the supply of histamine to the neurons, but instead may be in the ability of the neurons to effectively metabolize histamine into histamine $H_2$.

To illustrate this, Table C shows the sequential steps in the production and metabolism of histamine to yield histamine $H_2$.

TABLE C

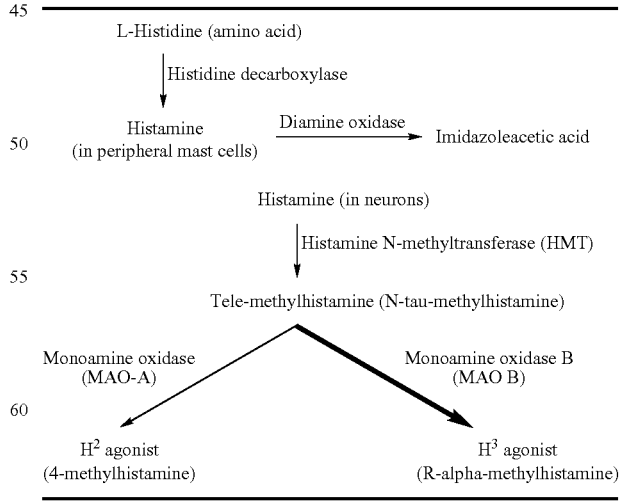

As can be seen, histamine is synthesized initially from L-histidine by the enzyme histidine decarboxylase. The histamine is stored in mast cells in the blood and most tissues in the body. Histamine that is released from mast cells results in an allergic response.

Histamine outside the brain is converted to imidazoleacetic acid by diamine oxidase (histaminase) (Ganong, Review of Medical Physiology, 6th Ed., 1973, pp.185-86). Histamine in the brain is mostly methylated by histamine N-methyltransferase to form tele-methyihistamine. Monoamine oxidase metabolizes the tele-methyihistamine further into R-alpha-methylhistamine (an $H_3$ agonist) and 4-methyihistamine (an $H_2$ agonist) (Oishi, "Turnover of brain histamine and its changes by various drugs", Nippon Yakurigaku Zasshi, November 1988, 92:271-81).

Research shows that the histamine level in the cerebral spinal fluid of MS patients is 60% higher than that of controls, while the activity of histamine N-methyltransferase (HMT) is significantly lower than that of controls, tending to confirm that MS patients have an impaired histamine metabolism (Tuomisto et al, "Histamine and histamine-N-mehtyltransferase in the CSF of patients with multiple sclerosis", 1983). This is congruent with the findings from the study referred to above (which used an $H_2$ agonist and a phosphodiesterase inhibitor), in which 100% of the study subjects in the placebo group showed an overall increase in their whole blood histamine levels in the first 30 days. This elevated level of whole blood histamine persisted for the entire 90-day study in 80% of the placebo subjects (who did not receive the histamine $H_2$ agonist), and was probably due to the skin irritation caused by the citric acid placebo and transdermal patch. 95% of the verum group also experienced an elevation in their whole blood histamine in the first 30 days, but unlike the placebo group, for 80% of those showing initially elevated histamine levels, it was followed by a decrease in whole blood histamine. Those patients whose whole blood histamine level increased and then decreased the most significantly, experienced the most improvements in the symptoms tested.

These phenomena may be explained in that an $H_2$ agonist, such as that administered in the study, may decrease the histamine level by stimulating the Histamine N-methyltransferase activity. For example, in a study by Maroi et al ("Effect of reserpine on histamine metabolism in the mouse brain", March 1991, 256:967-72), reserpine, which can stimulate $H_2$ receptors, inhibited the histamine increase induced by a histamine N-methyltransferase inhibitor, while having no significant affect on a histidine decarboxylase inhibitor. Consequently, it is believed that the histamine $H_2$ agonist administered during the study caused the HMT system to increase HMT activity and thereby increase the metabolism of histamine, resulting in the observed decrease in whole blood histamine levels.

Therefore, based on the results of the 29-patient study and other research, it is postulated that an altered histamine metabolism is associated with MS and related neurodegenerative conditions, resulting in a decrease in the turnover of histamine, and therefore lower histamine $H_2$ levels, leading ultimately to inadequate cAMP production. This view is consistent with the results of the Tuomisto study referenced above, which showed that the histamine level in MS patients was 60% higher than in non-MS patients while the activity of the enzyme, HMT, was significantly lower than in controls.

The study results set forth above also suggest that the problem with the metabolism of histamine in MS patients probably does not lie in the histidine decarboxylase enzyme activity, but rather in the activity of HMT or the monoamine oxidase enzymes, since it is clear the MS patients in the study were capable of producing whole blood histamine. MS patients are therefore apparently able to produce histamine from L-histidine via the enzymatic activity of histidine decarboxylase, but further metabolism of histamine in the neurons is impaired. This impaired neuron histamine metabolism may be due to either inadequate HMT activity or impaired MAO activity, or possibly both.

i. HMT Activity

Inadequate HMT activity may be the result of impaired synthesis of the enzyme. Based on this etiology, HMT levels may be beneficially supplemented by administration of the compound itself, i.e., by injections or other administration of the HMT enzyme. For example, HMT isolated as described in U.S. Pat. No. 4,769,322 (to Eli Lilly & Co.) may be administered parenterally, such as by intramuscular or subcutaneous injections, and possibly via transdermal application or oral administration.

ii. MAO Activity

As explained above, reduced metabolism of histamine may also be the result of impaired monoamine oxidase (MAO) activity.

Inadequate activity of monoamine oxidase-A and/or monoamine oxidase-B can result in an accumulation of tele-methylhistamine, which in turn causes an inhibition of HMT and an accumulation of histamine. As is indicated by the bold arrow in Table C, tele-methyihistamine is primarily metabolized via monoamine oxidase B (MAO-B) into an $H_3$ agonist (R-alpha-methylhistamine) (Elsworth et al, "Tele-methyihistamine is a specific MAO-B substrate in man", Psychopharmacology, 1980, 69:287-90). The release of histamine is regulated by $H_3$ autoreceptors (Prast et al., "In vivo modulation of histamine release by autoreceptors and muscarinic acetyicholine receptors in the rat anterior hypothalamus", Naunyn Schmiedebergs Arch Pharmacol, December 1994, 350:599-604). Tele-methylhistamine is metabolized by a second path into an $H_2$ agonist (4-methyihistamine), via monoamine oxidase A (MAO-A). Hence, the relative amounts of $H_2$ and $H_3$ agonists produced depends primarily on the relative activity of the MAO-A and MAO-B metabolic paths.

The MAO-A:MAO-B activity ratio is genetically encoded on the X chromosome (Garpenstrand et al, "Platelet monoamine oxidase activity is related to MAOB intron 13 genotyp", J. Neural Transm, 2000, 107:523-30). Interestingly, MS is more predominant in females than males. Estrogen and aging also selectively affect the synthesis of MAO-A. Estrogen decreases MAO-A activity in the hypothalamus, but does not affect the activity of MAO-B (Edelstein & Breakefield, "Monamine oxidases A and B are differentially regulated by glucocorticoids and "aging" in human skin fibroblasts", Cell Mol Neurobiol, June 1986, 6:121-50). The MAO-A:MAO-B activity ratios also decrease in all regions of the brain during maturational development in rats, and research has shown that the ontogenetic development of MAO-A and MAO-B in the human brain is parallel to that observed in the rodent brain (Strolin et al, "Developmental aspects of the monoamine-degrading enzyme monoamine oxidase", Dev Pharmacol Ther, 1992, 18:191-200).

As the MAO-A:MAO-B activity ratio decreases, metabolism of tele-methylhistamine via MAO-B becomes more dominant and MAO-A activity is inhibited. Elevated activity of MAO-B is associated with neurodegenerative disorders such as Parkinson and Alzheimer's diseases (Carlo et al, "Monoamine oxidase B expression is selectively regulated by dexamethasone in cultured rat astrocytes", Brain Res, March 1996, 4:175-83). Inhibition of MAO-A activity also results in a significant decrease in the responsiveness of the noradrenergic cyclic AMP generating system (Mishra et al, "Effect of selective monamine oxidase inhibition by clorgyline and deprenyl on the norepinephrine receptor-couple adenylate cyclase system in rat cortex", Psychopharmacology, 1983, 81:220-3). The $H_2$ agonist (4-methyihistamine) is the metabolite of tele-methyihistamine via MAO-A and is a potent stimulator of cyclic AMP synthesis. Thus, a decrease in MAO-A activity results in decreased $H_2$ receptor stimulation, which results in decreased cAMP production. As stated above, deficient cAMP production is believed to be directly involved in demyelination in MS and similar neurodegenerative conditions.

Other contributors to MAO-A inhibition may include stress. It is known that exacerbations or worsening of symptoms in MS patients are often triggered by stress. Research shows that stress stimulates the release of endogenous MAO-A inhibitors (Glover, "Function of endogenous monoamine oxidase inhibitors (tribulin), J Neural Transm Suppl, 1998, 52:307-13). Stress may thus be an added factor in the endogenous inhibition of an already deficient activity of MAO-A.

Lipid peroxidation is also known to inhibit the monoamine oxidase system (Medvedev et al, "The role of lipid peroxidation in the possible involvement of membrane-bound monoamine oxidases in gamma-aminobutyric acid and glucosamine deamination in rat brain. Focus on chemical pathogenesis of experimental audiogenic epilepsy", Mol Chem Neuropathol, February-April 1992, 16:187-201). MS patients have low levels of copper and zinc as discussed earlier, which debilitates the Cu-Zn-superoxide dimutase enzyme. Inhibition of this enzyme results in an increase in superoxide and nitric oxide which results in the formation of peroxinitrites, a free radical that leads to myelin destruction in MS (Johnson, "The possible role of gradual accumulation of copper, cadmium, lead and iron and gradual depletion of zinc, magnesium, selenium, vitamins B2, B6, D, and E and essential fatty acids in multiple sclerosis", September 2000, 55:239-41). Deficient levels of copper in MS patients also interferes with the synthesis of the monoamine oxidases themselves, because they are copper-containing enzymes.

A decrease in MAO-A activity caused by one or more of the mechanisms described above will decrease the MAO-A:MAO-B ratio. The resulting disproportion of the MAO-A:MAO-B ratio results in a parallel disproportion in the production ratio of the $H_2$ agonist (4-methylhistamine) to the $H_3$ agonist (R-alpha-methylhistamine). Increased production of the $H_3$ agonist (R-alpha-methylbistamine) then further inhibits MAO-A activity, compounding the $H_2$ deficiency.

Inhibition of MAO-B activity would increase the MAO-A:MAO-B activity ratio, thereby increasing histamine $H_2$ levels. An $H_3$ antagonist such as thioperamide maleate inhibits MAO-B (Sakurai et al, "Effects of the histamine $H_3$ agonist (R)-alpha-methylhistamine and the antagonist thioperamide in vitro on monoamine oxidase activity in the rat brain", Exp Clin Pharmacol, November 1995, 17C:46-50). It may therefore be beneficial to administer an $H_3$ antagonist such a thioperamide maleate in order to increase the MAO-A:MAO-B activity ratio. Thioperamide maleate is available in suitable form from VWR Scientific Products, a company of the Merck Group.

It may also be beneficial to administer MAO-A agonists such as reserpine. Reserpine oxidizes serotonin and is therefore similar in action to MAO-A, since MAO-A also oxidizes serotonin (Benedetti & Keane, "Differential changes in monoamine oxidase A and B activity in the aging rat brain", J Neurochem, November 1980, 35:1026-32). Injecting reserpine in dosages of about 1-10 mg/kg S.C. per day, or using a slow release transdermal dose, will be sufficient in most instances to increase the metabolism of tele-methylhistamine to a histamine $H_2$ agonist, e.g., 4-methylbistamine, resulting in adequate $H_2$ receptor stimulation. Reserpine is available in suitable form from VWR Scientific Products.

It is to be recognized that various alterations, modifications, and/or additions may be introduced into the constructions and arrangements of parts described above without departing from the spirit or ambit of the present invention.

What is claimed is:

1. A method for therapeutic treatment of multiple sclerosis, said method comprising the steps of:

administering to a patient in need thereof monoamine oxidase-A effective for increasing neuronal metabolism of histamine to a histamine $H_2$ agonist, in an amount sufficient that said histamine $H_2$ agonist is produced in an amount adequate to stimulate production of cyclic AMP at a level which maintains myelin against undergoing self-degeneration;

the step of administering said compound comprising administering monoamine oxidase-A to said patient in accordance with a regimen that provides a predetermined daily dosage of said monoamine oxidase-A so as to increase neuronal metabolism of tele-methylhistamine to an $H_2$ agonist.

2. A method for therapeutic treatment of multiple sclerosis, said method comprising the steps of:

administering to a patient in need thereof monoamine oxidase-A agonist effective for increasing neuronal metabolism of histamine to a histamine $H_2$ agonist, in an amount sufficient that said histamine $H_2$ agonist is produced in an amount adequate to stimulate production of cyclic AMP at a level which maintains myelin against undergoing self-degeneration;

the step of administering said monoamine oxidase-A agonist comprising administering said monoamine oxidase-A agonist to said patient in accordance with a regimen that provides a predetermined daily dosage of said monamine oxidase-A agonist so as to increase neuronal metabolism of tele-methylhistamine to an $H_2$ agonist.

3. The method of claim 2, wherein said monoamine oxidase-A agonist is reserpine.

4. The method of claim 3, wherein the step of administering said monoamine oxidase-A agonist comprises:

administering reserpine by slow-release transdermal dose.

5. The method of claim 2, wherein the step of administering said monoamine oxidase-A agonist comprises:

administering reserpine by injection in the range from about 1-10 mg/kg S.C. per day.

* * * * *